United States Patent
Mostofi-Ashtiani et al.

(10) Patent No.: US 11,261,143 B2
(45) Date of Patent: Mar. 1, 2022

(54) APPARATUS AND PROCESS FOR SEPARATING GASES FROM CATALYST

(71) Applicant: UOP LLC, Des Plaines, IL (US)

(72) Inventors: Mohammad Reza Mostofi-Ashtiani, Naperville, IL (US); Lev Davydov, Northbrook, IL (US); Robert Mehlberg, Wheaton, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 16/839,017

(22) Filed: Apr. 2, 2020

(65) Prior Publication Data

US 2020/0325087 A1 Oct. 15, 2020

Related U.S. Application Data

(60) Provisional application No. 62/833,292, filed on Apr. 12, 2019.

(51) Int. Cl.
*C07C 7/00* (2006.01)
*B01J 8/00* (2006.01)
*B01J 8/18* (2006.01)

(52) U.S. Cl.
CPC ............ *C07C 7/005* (2013.01); *B01J 8/0055* (2013.01); *B01J 8/1827* (2013.01); *B01J 8/1863* (2013.01); *B01J 2208/00761* (2013.01)

(58) Field of Classification Search
CPC .... C10G 11/18; C10G 2300/4093; B01J 8/34; B01J 8/0055; B01J 38/04; B01J 19/32; B01J 2219/32282; B01J 8/005; B01J 8/12; B01J 8/125; B01J 8/1872; B01J 8/26; B01D 53/10
USPC ........................................ 422/144, 145, 147
See application file for complete search history.

(56) References Cited

U.S. PATENT DOCUMENTS

| | | |
|---|---|---|
| 7,799,286 B2 | 9/2010 | Mehlberg |
| 2009/0107884 A1* | 4/2009 | Mehlberg ............... C10G 11/18 208/113 |

* cited by examiner

*Primary Examiner* — Sharon Pregler
(74) *Attorney, Agent, or Firm* — Paschall & Associates, LLC; James C. Paschall

(57) ABSTRACT

In an FCC apparatus in which swirl arms are used to discharge gas and catalyst from a riser, the swirling movement of the catalyst particles is inhibited while impeding the catalyst particles and gaseous products from exiting the disengaging chamber and entering a reactor annulus. The catalyst particles and gaseous products pass through a tunnel comprising a vertical wall to enter the reactor annulus. The vertical wall presents a face that is opposed to the angular direction in which the catalyst particles and gaseous products swirl.

A baffle may be located at the intersection between the reactor annulus and the disengaging chamber to deflect catalyst laterally in a stripping section after exiting the reactor annulus. The baffle may be equipped with openings to fluidize the large proportion of catalyst passing over this region to effectively pre-strip this catalyst before it enters a stripping section.

20 Claims, 2 Drawing Sheets

APPARATUS AND PROCESS FOR SEPARATING GASES FROM CATALYST

CROSS-REFERENCE TO RELATED APPLICATIONS

This application claims priority from provisional application 62/833,292, filed Apr. 12, 2019, incorporated herein in its entirety.

FIELD

The field is processes and apparatuses for the fluidized contacting of catalyst with hydrocarbons. More specifically, the field is processes and apparatuses for separating entrained product hydrocarbon gases from catalyst particles.

BACKGROUND

Fluid catalytic cracking (FCC) is a process that contacts hydrocarbons in a reaction zone with a catalyst composed of finely divided particulate material. The hydrocarbon feed and fluidizing gases, such as steam, fluidize the catalyst and typically transport it in a riser as the catalyst promotes the cracking reaction. As the cracking reaction proceeds, substantial amounts of hydrocarbon, called coke, are deposited on the catalyst. A high temperature regeneration within a regeneration vessel burns coke from the catalyst by contact with an oxygen-containing stream that again serves as a fluidization medium. Coke-containing catalyst, referred to herein as spent catalyst, is continually removed from the reaction zone and replaced by coke-free or reduced coke catalyst from the regeneration zone. Fluidization of the catalyst particles by various gaseous streams allows the transport of catalyst between the reaction zone and regeneration zone.

In the FCC process, gaseous fluids are separated from particulate catalyst solids as they are discharged from a reactor riser. The most common method of separating particulate solids from a gas stream uses centripetal separation in a disengagement vessel. Centripetal separators operate by imparting a tangential velocity to gases containing entrained solid particles that forces the heavier solids particles outwardly away from the lighter gases for upward withdrawal of gases and downward collection of solids. An exit from a riser conduit comprises an arcuate, tubular swirl arm which imparts a swirling, helical motion to the product gases and particulate catalyst as they discharge from the riser into a disengaging chamber. The swirling, helical motion of the materials in the separation vessel effects an initial separation of the particulate catalyst from the gases. The initial stage of separation is typically followed by a second more compete separation of solids from gases in cyclones. A gas recovery conduit communicates the disengaging chamber with cyclones in a reactor vessel. The mixture of gases and entrained catalyst is drawn up the gas recovery conduit and fed into cyclones to effect further separation of the particulate catalyst from the gases.

A majority of the hydrocarbon vapors that contact the catalyst in the reaction zone are separated from the solid particles by the aforementioned centripetal separation. However, the catalyst particles employed in an FCC process have a large surface area, which is due to a great multitude of pores located in the particles. As a result, the catalytic materials retain hydrocarbons within their pores, upon the external surface of the catalyst and in the spaces between individual catalyst particles as they enter the stripping zone. Although the quantity of hydrocarbons retained on each individual catalyst particle is very small, the large amount of catalyst and the high catalyst circulation rate which is typically used in a modern FCC process results in a significant quantity of hydrocarbons being withdrawn from the reaction zone with the catalyst.

It is common practice to remove, or strip, hydrocarbons from spent catalyst prior to passing it into the regeneration zone. The most common method of stripping the catalyst passes a stripping gas, usually steam, through a flowing stream of catalyst, counter-current to its direction of flow. Such steam stripping operations, with varying degrees of efficiency, remove the hydrocarbon vapors which are entrained with the catalyst and adsorbed on the catalyst.

The efficiency of catalyst stripping is increased by using stripping internals which may comprise vertically spaced baffles or patterned strips to cascade the catalyst from side to side as it moves down a stripping apparatus and counter-currently contacts a stripping medium. The stripping medium enters from below the lower internals and continues rising upwardly through the internals.

Catalyst discharged from a swirl exit of a riser to separate the spent catalyst from product gases may continue to swirl. The swirling descending catalyst can potentially cause erosion of internal equipment and flow maldistribution in the stripping section. Consequently, the dense catalyst bed is afforded sufficient height above the stripping internals to buffer the stripping internals from erosion by the swirling catalyst.

BRIEF SUMMARY OF THE INVENTION

We have discovered a way to break or dampen the rotational flow of catalyst inside and outside of a disengaging chamber that utilizes a tangential discharge of catalyst and product gases from a riser. The swirling catalyst particles are inhibited from exiting the disengaging chamber and entering a reactor annulus. The catalyst particles and gaseous products are required to pass through a tunnel comprising a vertical wall to enter the reactor annulus. The vertical wall presents a face that is opposed to the angular direction in which the catalyst particles and gaseous products swirl. Consequently, the angular momentum of the catalyst particles and gaseous products is reduced. Moreover, the tunnel will not allow catalyst particles and gaseous products to enter the reactor annulus unless they change direction. Instead, the catalyst particles fall into the stripping section.

We have also found that a large proportion of catalyst particles pass over lower edges of passages between the disengaging chamber and the reactor annulus. Consequently, a baffle may be located at the intersection between a reactor annulus and a disengaging chamber to deflect catalyst laterally in a stripping section after descending below a passage to the reactor annulus. The baffle may be equipped with openings to fluidize the large quantity of catalyst passing over this region to effectively pre-strip this catalyst before it enters a stripping section.

Additional details and embodiments of the invention will become apparent from the following detailed description of the invention.

DESCRIPTION OF THE INVENTION

Figure 1:
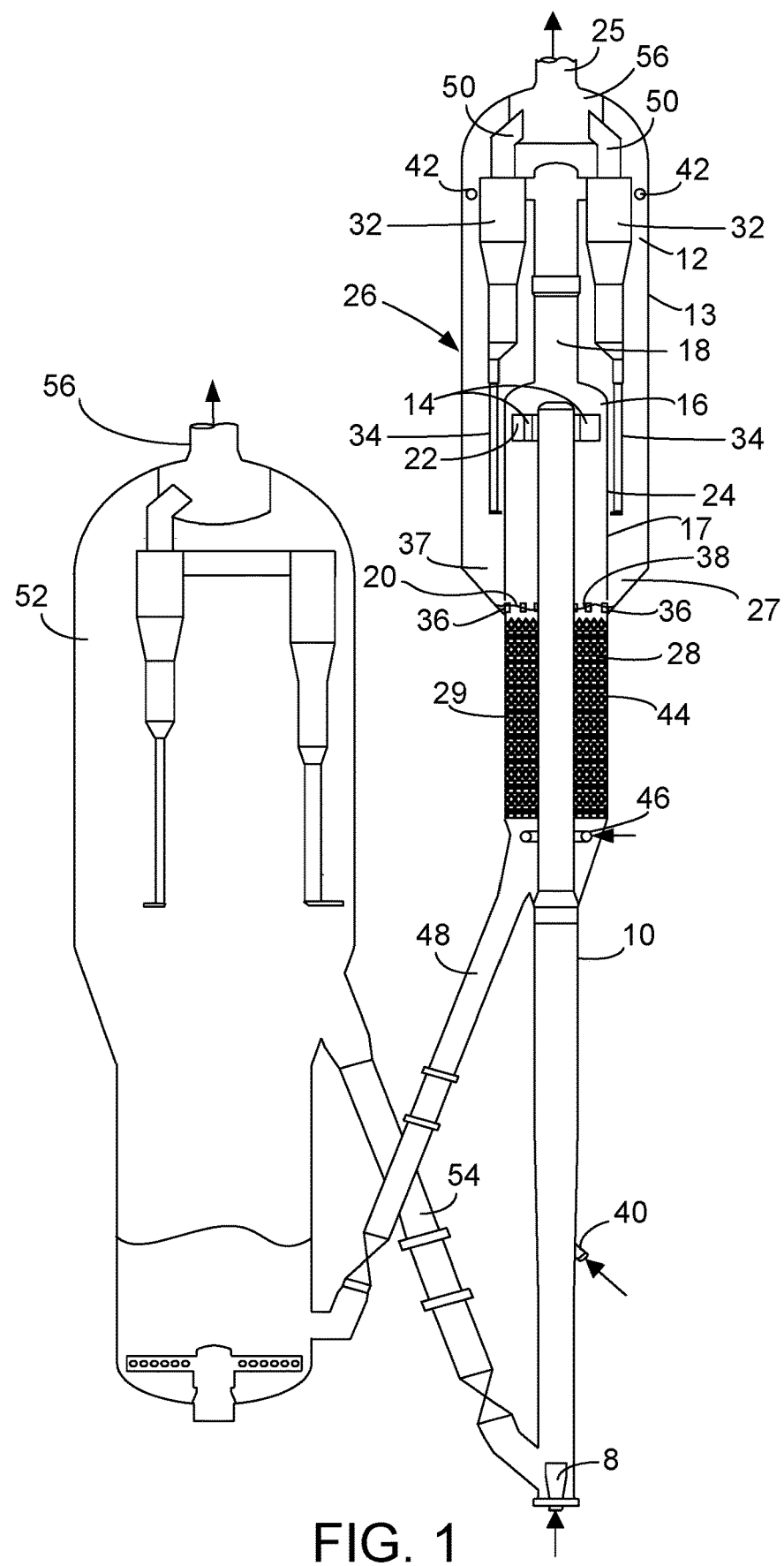
FIG. 1 is a schematic cross-sectional view of an FCC unit.

Tangential or swirl arms that effect primary separation of catalyst and gaseous products discharged from a FCC riser reactor imparts substantial tangential momentum to catalyst particles. As they descend down a disengaging chamber, we have found the swirling gas and catalyst generates a rotating catalyst bed. This behavior causes extensive erosion of the top layers of stripping internals in specific locations spaced from each in a way that corresponds to the spacing of the swirl arm outlets from the riser.

We have also observed in commercial operation that greater residence time in the dense catalyst bed above the stripping section results in lower product yield. This may result from cracking reactions continuing to occur while the product gases are in contact with catalyst. Reducing the depth of the dense catalyst bed to reduce product gas residence time would be advantageous. However, to do so, the rotational momentum of the catalyst particles and gaseous products have to be mitigated because the dense catalyst bed serves to buffer the top stripping internals from abrasion by swirling catalyst currents.

We propose to inhibit the swirling catalyst particles from exiting the disengaging chamber and entering a reactor annulus. The catalyst particles and gaseous products are required to pass through a tunnel comprising a vertical wall to enter the reactor annulus. The vertical wall presents a face that is opposed to the angular direction in which the catalyst particles and gaseous products swirl. In order to exit the disengaging chamber through the tunnel, the flow will have to change its tangential direction, then maintain that new direction for the width of the vertical wall, and then enter the reactor annulus around the disengaging chamber. This way, the tangential momentum carried from the riser discharge arms to the dense annular bed can be mitigated, entry of catalyst into the reactor annulus is reduced and unwanted hardware erosion or catalyst short-circuiting can be avoided.

The apparatus or process may be conducted in a fluid catalytic cracking (FCC) operation in which catalyst particles and gaseous products must be separated. The typical feed to an FCC unit is a gas oil such as a vacuum gas oil or atmospheric residue.

As used herein, the term "boiling point temperature" means atmospheric equivalent boiling point (AEBP) as calculated from the observed boiling temperature and the distillation pressure, as calculated using the equations furnished in ASTM D1160 appendix A7 entitled "Practice for Converting Observed Vapor Temperatures to Atmospheric Equivalent Temperatures". As used herein, the term "True Boiling Point" (TBP) means a test method for determining the boiling point of a material which corresponds to ASTM D-2892 for the production of a liquefied gas, distillate fractions, and residuum of standardized quality on which analytical data can be obtained, and the determination of yields of the above fractions by both mass and volume from which a graph of temperature versus mass % distilled is produced using fifteen theoretical plates in a column with a 5:1 reflux ratio. As used herein, the term "T5" or "T95" means the temperature at which 5 mass percent or 95 mass percent, as the case may be, respectively, of the sample boils using ASTM D-86 or TBP. As used herein, the term "initial boiling point" (IBP) means the temperature at which the sample begins to boil using ASTM D-7169, ASTM D-86 or TBP, as the case may be. As used herein, the term "end point" (EP) means the temperature at which the sample has all boiled off using ASTM D-7169, ASTM D-86 or TBP, as the case may be. As used herein, "vacuum gas oil" means a hydrocarbon material having an IBP of at least about 232° C. (450° F.), a T5 of between about 288° C. (550° F.) and about 392° C. (700° F.), typically no more than about 343° C. (650° F.), a T95 between about 510° C. (950° F.) and about 570° C. (1058° F.) and, or an EP of no more than about 626° C. (1158° F.) prepared by vacuum fractionation of atmospheric residue as determined by any standard gas chromatographic simulated distillation method such as ASTM D2887, D6352 or D7169, all of which are used by the petroleum industry. As used herein, "atmospheric residue" means a hydrocarbon material having an IBP of at least about 232° C. (450° F.), a T5 of between about 288° C. (550° F.) and about 392° C. (700° F.), typically no more than about 343° C. (650° F.), and a T95 between about 510° C. (950° F.) and about 700° C. (1292° F.) obtained from the bottoms of an atmospheric crude distillation column.

The reaction zone of an FCC process is maintained at high temperature conditions which may generally include a temperature above about 425° C. (797° F.). In an embodiment, the reaction zone is maintained at cracking conditions which include a temperature of from about 480° C. (896° F.) to about 590° C. (1094° F.) and a pressure of from about 69 kPa (g) (10 psig) to about 517 kPa (g) (75 psig) but typically less than about 275 kPa (g) (40 psig). The catalyst-to-oil ratio, based on the weight of catalyst and feed hydrocarbons entering the bottom of the riser, may range up to 20:1 but is typically between about 4:1 and about 10:1. Hydrogen is not normally added to the riser generating an absence of substantial added hydrogen in the reactor. Steam is typically passed into the riser to effect catalyst fluidization and feed dispersion. The average residence time of catalyst in the riser may be less than about 5 seconds. The type of catalyst employed in the process may be chosen from a variety of commercially available catalysts. A catalyst comprising a Y-type zeolite base material is preferred, but the older style amorphous catalyst may be used if desired. MFI zeolite may be added to the catalyst mixture.

The catalyst regenerator is preferably operated at a pressure of from about 69 kPa (g) (10 psig) to about 552 kPa (g) (80 psig). The spent catalyst being charged to the regenerator may contain from about 0.2 to about 15 wt-% coke. This coke is predominantly comprised of carbon and can contain from about 3 to about 12 wt-% hydrogen, as well as sulfur and other elements. The oxidation of coke will produce the common combustion products: water, carbon oxides, sulfur oxides and nitrous oxides. The regenerator may take several configurations, with regeneration being performed in one or more stages.

FIG. 1 is the schematic illustration of an FCC unit. The FCC unit includes an elongated riser or reactor riser 10. Hot catalyst is delivered to a lower section of the riser 10 from a regenerator conduit 54 at which a fluidizing gas from a distributor 8 pneumatically conveys the catalyst particles upwardly through the riser 10. As the mixture of catalyst and conveying gas continues up the riser 10, a nozzle 40 injects hydrocarbonaceous feed and perhaps steam into the catalyst. The contact with hot catalyst vaporizes the hydrocarbons and further conveys the mixture of gas and catalyst through the riser 10 while cracking the hydrocarbons to desirable lower-boiling, gaseous products.

The riser 10 extends upwardly into a reactor vessel 12. The riser 10 preferably has a vertical orientation within the reactor vessel 12 and may extend upwardly through a bottom of the reactor vessel 12. The reactor vessel comprises an outer wall 13. The catalyst particles and gaseous products are then discharged from the top of the reactor riser 10 and separated into a cracked gaseous products and catalyst particles covered with substantial quantities of coke and generally referred to as "spent catalyst." A swirl arm arrangement 26 is provided at the discharge end of the reactor riser 10 for enhanced initial separation of catalyst particles from cracked gaseous products. The swirl arm arrangement 26 includes a curved tubular arm 14 that induces the solid catalyst particles and gaseous products to swirl in an angular direction, imparting a tangential angular velocity to the exiting mixture of catalyst particles and cracked gaseous products as they are discharged from a swirl outlet 22. The swirl arm arrangement 26 may be located in an upper region of a disengaging chamber 16. The disengaging chamber 16 comprises an outer shell 17. The swirl arm arrangement 26 may comprise a plurality of arms 14 with a corresponding number of swirl outlets 22. The disengaging chamber 16 is in downstream communication with the swirl outlet 14. The term "communication" means that fluid flow is operatively permitted between enumerated components. The term "downstream communication" means that at least a portion of fluid flowing to the subject in downstream communication may operatively flow from the object with which it fluidly communicates. A stripping section 28 may be located in the disengaging chamber 16 below the swirl outlet 26. Catalyst separated by the swirl arm arrangement 26 drops down into the stripping section 28. The stripping section 28 includes an outer wall 29.

The cracked gaseous products, comprising cracked hydrocarbons and entrained spent catalyst particles, exit the disengaging chamber 16 via a gas recovery conduit 18. Cyclones 32 are in downstream communication with the swirl outlet 22 via the gas recovery conduit 18. The cyclones 32 create a tangential swirling motion therein to establishes centripetal forces that further separates solids from gases. A product gas stream, relatively free of catalyst particles, exits the cyclones 32 through vapor outlet pipes 50 into a plenum chamber 56. The product stream then exits the reactor vessel 12 through an outlet 25. Catalyst solids recovered by the cyclones 32 exit the bottom of the cyclone through diplegs 34. The diplegs 34 extend downwardly in the reactor vessel 12 and may terminate at a flapper valve which prevents gas from entering the dipleg 34 but allows catalyst particles to exit into a dense bed 20 at a bottom of the reactor vessel 12 surrounding the disengaging chamber 16 comprising a reactor annulus 37.

Catalyst particles in the reactor vessel 12 are admitted by passages 36 into the disengaging chamber 16. The passages 36 may comprise windows between the reactor vessel 12 and the disengaging chamber 16 to allow catalyst to flow from the reactor annulus 37 into the disengaging chamber 16. The disengaging chamber 16 is in downstream communication with the reactor vessel 12 and/or the cyclones therein through the passages 36 due to and head pressure. Catalyst particles in the dense catalyst bed 20 enter the stripping section 28 located in the disengaging chamber 16. Catalyst particles pass downwardly through and/or over stripping internals 44 which may comprise a plurality of elongated metal strips arranged together in a pattern in the stripping section 28. The strips may have straight portions set at angles to other strips or other straight portions of the same strip. Layers or arrays of strips may be stacked in the stripping section. The metal strips may define a structural packing or may define gratings with or without downcomers. Examples of suitable structural packing may be found in US 2005/0205467 and suitable gratings may be found in U.S. Pat. No. 6,680,030 for use in stripping vessels.

A stripping fluid, typically steam, enters a lower portion of the stripping section 28 through at least one distributor 46. Counter-current contact of the catalyst with the stripping fluid over the metal strips 44 displaces product gases adsorbed on the catalyst as it continues downwardly through the stripping section 28. Stripped catalyst from the stripping section 28 may pass through a spent catalyst conduit 48 to a catalyst regenerator 52. In the regenerator, coke deposits are combusted from the surface of the catalyst by contact with an oxygen-containing gas at high temperature. Following regeneration, regenerated catalyst particles are delivered back to the bottom of the riser 10 through the regenerator conduit 54. Flue gas exits the regenerator 52 through nozzle 56.

We have found that the swirling motion induced by the product gases and catalyst particles issuing from the swirl outlet(s) 22 of the riser 10 may continue as the catalyst descends in the disengaging chamber 16. The swirling gas and catalyst generates a rotating catalyst bed 20 that can cause extensive erosion of the top layers of stripping internals and bypass some or all of the stripping section 28.

Figure 2:
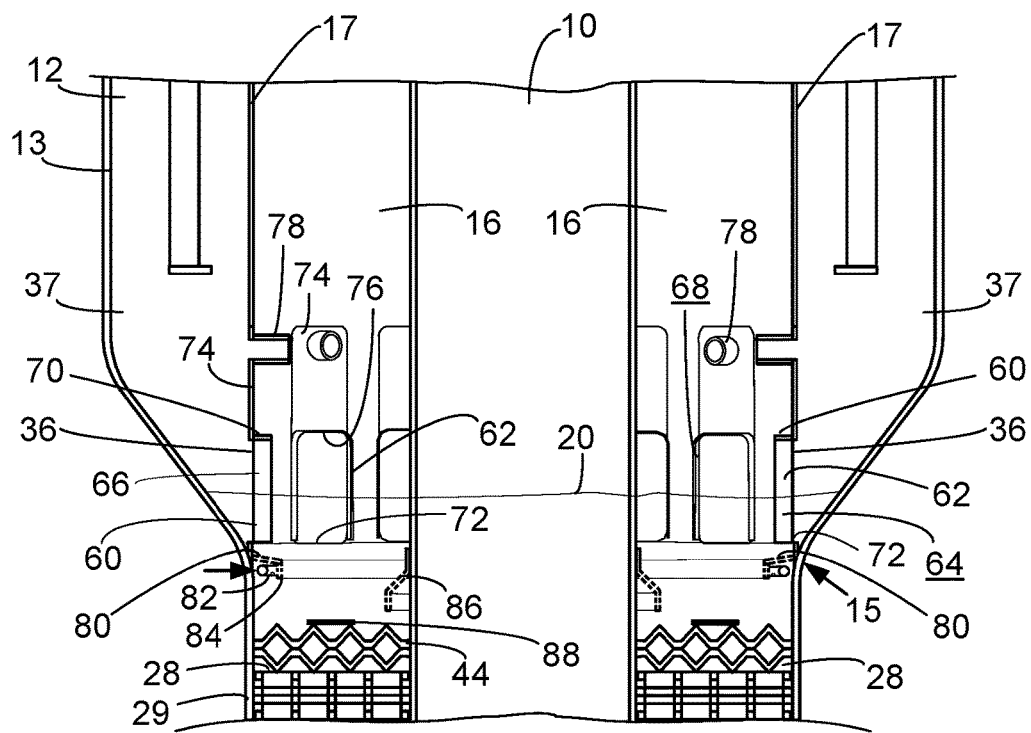
FIG. 2 is an enlarged partial view of a portion of FIG. 1.

We propose a process and apparatus that mitigates or dampens the angular momentum of the descending catalyst particles and gaseous products in the disengaging chamber 16. The process and apparatus are further illustrated with reference to FIG. 2 which is an enlarged partial version of a bottom of the disengaging chamber 16 of FIG. 1. The swirling catalyst particles and gaseous products descend in the disengaging chamber in a rotational vortex. Some of the catalyst particles and gaseous products tend to exit the passages 36 arrayed around the circumference of the disengaging chamber. The passages 36 are equipped with tunnels 60 that communicate the disengaging chamber 16 with the reactor annulus 37 and vice-versa. The tunnels 60 inhibit the swirling of the catalyst particles and gaseous products and impede the catalyst particles and gaseous products from exiting the disengaging chamber 16 and entering the reactor annulus 37. The tunnel 60 and passages 36 still provide a large opening that allows pressure relief in the event of a pressure surge in the system.

The tunnel 60 comprises at least a first vertical wall 62 that presents a face 64 that is oriented to oppose the angular direction in which the catalyst particles and gaseous products swirl. The first vertical wall 62 has a width that provides the face 64 that can block and resist the angular momentum of the swirling catalyst particles and gaseous products. The first vertical wall 62 may provide the face 64 that resists angular momentum on its outer surface. In an embodiment, the first vertical wall 62 extends radially in the disengaging chamber 16. In a further embodiment, the first vertical wall 62 extends inwardly from the shell 17 in the disengaging chamber 16.

In an embodiment, the tunnel 60 comprises at a second vertical wall 66 that presents a face 68 that is oriented to oppose the angular direction in which the catalyst particles and gaseous products swirl. The second vertical wall 66 has a width that provides the face 68 that can block and resist the angular momentum of the swirling catalyst particles and gaseous products. The second vertical wall 66 may provide the face 68 that resists angular momentum on its inner surface. In an embodiment, the second vertical wall 66 extends radially in the disengaging chamber 16. In a further embodiment, the second vertical wall 66 extends inwardly from the shell 17 in the disengaging chamber 16.

In an additional embodiment, the tunnel 60 comprises a top horizontal wall 70 located upwardly of the first vertical wall 62 and said second vertical wall 66. In an aspect, the top horizontal wall 70 is at a top of the tunnel 60. In a further aspect, the top horizontal wall is above the first vertical wall 62 and the second vertical wall 66. The top horizontal wall 70 of the tunnel 60 may overhang the passage 36. The tunnel 60 may lack a lower horizontal wall that would be opposed to the top horizontal wall 70, so that the tunnel 60 defines an inverted U.

In operation, swirling catalyst particles and gaseous products descend downwardly in the disengaging chamber 16 and encounter the face 64 of the first vertical wall 62 and the face 68 of the second vertical wall 66 which opposes the rotational direction of swirl and blocks and reduces the angular momentum of the catalyst particles and product gases. Some of the catalyst particles and product gases will still exit the disengaging chamber 16 through the passages 36 and enter the reactor annulus 37, but the tunnel 60 will reduce the volume of entry into the passages because the swirling catalyst particles and gaseous products will have to change direction from swirling and travel radially outwardly through the tunnel 60 comprising the first vertical wall 62, the second vertical wall 66 and/or the top horizontal wall 70.

The passage 36 has a lower edge 72 that is located at an intersection 15 of a wall 13 of the reactor vessel 12 and the shell 17 of the disengaging chamber 16. The intersection may be termed as between the reactor annulus 37 and the disengaging chamber 16. The lower edge 72 may be located just above the intersection 15 but by a distance of no more than one-half riser diameter and preferably no more than one-quarter riser diameter. This location of the lower edge 72 of the passages 36 enables the top of the dense bed 20 to be located at a lower elevation in the disengaging vessel 16 thus reducing the height of the dense bed and reducing residence time of product gases in the dense bed. We have found that reduction of residence time of product gases in the dense bed 20 improves gasoline yield and reduces nonselective cracking of products.

To revamp passages 36 that are taller so as to further reduce entry of catalyst particles and gaseous products from exiting the disengaging chamber 16 through passages 36 into the reactor annulus 37 and to permit further reduction of the height of the dense catalyst bed 20, covers 74 may be secured to an upper region of passages 36. The covers 74 enable positioning a top edge 76 of the passages 36 at a lower height than if the covers were not installed. The covers 74 may be welded to the passages 36 or fastened in another suitable manner. Covers 74 may be equipped with a vent tube 78 to enable pressure surge relief in the event that a top of the catalyst bed 20 rises above the top edge 76 of the passages 36 and seals them off during a surge. Pressure relief will prevent damage to the equipment. The vent tubes 78 are located above the top edge 76 of the passages 36.

We have found that equipping the passages 36 with tunnels 60 with no lower wall, in an aspect, no lower wall opposed to the top horizontal wall 70, results in a large proportion of catalyst particles passing over the lower edge 72 of the passage 36. An intersection baffle 80 is provided below the tunnel 60. The intersection baffle 80 may extend from the intersection 15 of the wall 13 of the reactor vessel 12 and the shell 17 of the disengaging chamber 16 which may be termed as between the reactor annulus 37 and the disengaging chamber 16. The intersection baffle 80 may be located no more than one-eighth of a riser diameter from the intersection 15. The intersection baffle 80 extends into the disengaging chamber 16 at a slightly downward incline such as between 5 and 30 degrees from horizontal, preferably no more than 20 degrees. The intersection baffle 80 deflects catalyst particles moving downwardly laterally after passing through the tunnel 60 or upon entering into disengaging chamber 16 from the reactor annulus 37 below the tunnel. The intersection baffle 80 may deflect catalyst particles away from the outer wall 29 of the stripping section 28. The intersection baffle 80 may be an annular baffle that circumferences the entire disengaging chamber 12 above the stripping section 28. The top horizontal wall 70 overhangs the intersection baffle 80, so as to channel catalyst particles over the baffle as it enters said disengaging chamber 16 from the tunnel 60 and/or the reactor annulus 37.

The intersection baffle 80 may further include openings in the baffle for emitting stripping gas to fluidize catalyst particles being deflected over the baffle with fluidizing gas. The large proportion of catalyst particles that travel over the intersection baffle 80 are effectively pre-stripped just before they descend and enter into the stripping section 28. A distributor ring 82 may be located directly below the intersection baffle 80 for distributing stripping gas such as steam below the intersection baffle 80. We have found that pre-stripping catalyst at this location reduces mean residence time of gasoline vapors intermingled with catalyst particles in the stripping section 28. By deflecting catalyst particles laterally, perhaps away from the outer wall 29 of the stripping section 28, and disrupting the rotational movement of the descending catalyst particles and gaseous products, the catalyst bed 20 can be reduced in height above the stripping section 28 while still protecting the top of the stripping internals 44 from erosion. The intersection baffle 80 may include a vertical weir 84 that depends vertically from the intersection baffle 80. The weir 84 may also be equipped with openings to fluidize catalyst falling down the weir.

An additional riser baffle 86 may be located on the riser 10 in the disengaging chamber 16 at a location at a projection following the incline of the intersection baffle 80 across the disengaging chamber from the shell 17 to the riser 10. The riser baffle 86 may be located above the stripping internals 44 and be equipped with openings for fluidization, a depending weir and may optionally be equipped with a steam ring under the riser baffle 82 (not shown). The riser baffle 86 may have a greater slope than the intersection baffle 80 such as between 30 and 70 degrees from horizontal. The riser baffle may be annular and circumference the entire riser 10. Additionally, a splash plate 88 may be located above the stripping section 28 on top of the stripping internals 44 at its annular center to protect the internals from catalyst directed at it by the intersection baffle 80 and the riser baffle 86. The splash plate 88 may be annular as well.

Figure 3:
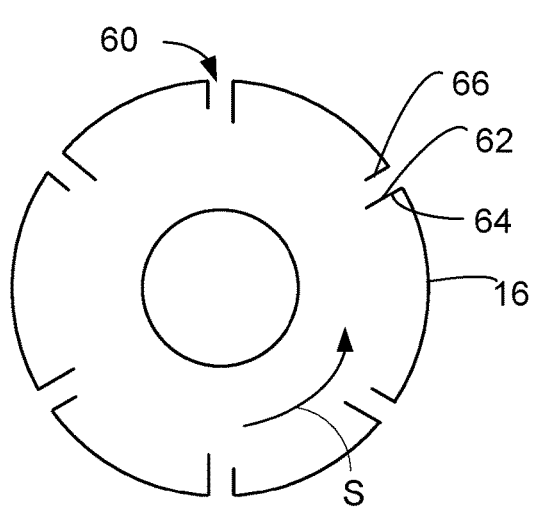
FIG. 3 is a plan schematic of an alternative to FIG. 2.

FIG. 3 shows an additional embodiment of the disengaging chamber 16 comprising tunnels 60. The first vertical wall 62 that presents the outer face 64 to the direction of swirl S is wider than the second vertical wall 66.

Figure 4:
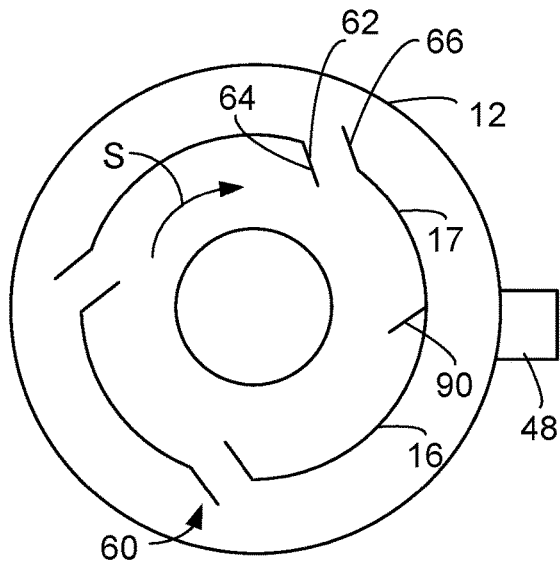
FIG. 4 is a plan schematic of another alternative to FIG. 2.

FIG. 4 shows an additional embodiment of the disengaging chamber 16 comprising tunnels 60 surrounded by the reactor vessel 12. The direction of swirl is in the opposite direction as in FIG. 3. The first vertical wall 62 extends more outwardly of the shell 17 of the disengaging chamber 16 than the second vertical wall 64 and the second vertical wall extends more inwardly of the shell than the first vertical wall. A vertical baffle 90 shields the spent catalyst conduit 48 from catalyst particles to prevent bypassing the stripping section.

The process and apparatus permits operating the FCC unit at a very low bed level without potential erosion of stripping internals. Testing has shown yield benefits of lower dry gas and higher gasoline selectivity.

Specific Embodiments

While the following is described in conjunction with specific embodiments, it will be understood that this description is intended to illustrate and not limit the scope of the preceding description and the appended claims.

A first embodiment of the invention is a process for separating catalyst particles from a gaseous product stream comprising contacting a hydrocarbon feed stream with catalyst particles in an elongated riser to produce gaseous products; inducing the catalyst particles and gaseous products to swirl in an angular direction upon exiting the riser and entering a disengaging chamber to disengage catalyst particles from the gaseous product; inhibiting the catalyst particles and gaseous products from exiting the disengaging chamber and entering a reactor annulus. An embodiment of the invention is one, any or all of prior embodiments in this paragraph up through the first embodiment in this paragraph further comprising requiring passage of the catalyst particles and the gaseous products through a tunnel with a vertical wall to exit the disengaging chamber and enter the reactor annulus. An embodiment of the invention is one, any or all of prior embodiments in this paragraph up through the first embodiment in this paragraph wherein the vertical wall of the tunnel presents a face opposed to the angular direction in which the catalyst particles and gaseous products swirl. An embodiment of the invention is one, any or all of prior embodiments in this paragraph up through the first embodiment in this paragraph further comprising stripping descending catalyst particles with a stripping gas over elongated strips in a stripping section; and separating catalyst particles entrained with ascending gaseous products from the gaseous products. An embodiment of the invention is one, any or all of prior embodiments in this paragraph up through the first embodiment in this paragraph further comprising deflecting downward movement of the catalyst particles laterally upon entering into the disengaging chamber from the tunnel. An embodiment of the invention is one, any or all of prior embodiments in this paragraph up through the first embodiment in this paragraph further comprising fluidizing the catalyst particles being deflected with fluidizing gas through openings in a deflecting baffle.

A second embodiment of the invention is an apparatus for separating catalyst particles from a gaseous product stream comprising an elongated riser in which a hydrocarbon feed is contacted with catalyst particles to produce a gaseous product, the riser including a swirl outlet configured to induce the solid catalyst particles and gaseous products to swirl in an angular direction to disengage catalyst particles from the gaseous product; a disengaging chamber communicating with the swirl outlet of the riser, the disengaging chamber including an outer shell and a stripping section comprising stripping internals; a tunnel comprising a vertical wall which communicates the disengaging chamber with a reactor annulus. An embodiment of the invention is one, any or all of prior embodiments in this paragraph up through the second embodiment in this paragraph wherein the vertical wall extends inwardly of the shell. An embodiment of the invention is one, any or all of prior embodiments in this paragraph up through the second embodiment in this paragraph wherein the tunnel comprises a first vertical wall and a second vertical wall. An embodiment of the invention is one, any or all of prior embodiments in this paragraph up through the second embodiment in this paragraph wherein the first vertical wall is wider than the second vertical wall. An embodiment of the invention is one, any or all of prior embodiments in this paragraph up through the second embodiment in this paragraph wherein the first wall extends more outwardly of the shell and the second wall extends more inwardly of the shell. An embodiment of the invention is one, any or all of prior embodiments in this paragraph up through the second embodiment in this paragraph wherein the tunnel comprises a top horizontal wall upwardly of the first vertical wall and the second vertical wall. An embodiment of the invention is one, any or all of prior embodiments in this paragraph up through the second embodiment in this paragraph further comprising a baffle below the tunnel that extends into the disengaging chamber at a downward incline. An embodiment of the invention is one, any or all of prior embodiments in this paragraph up through the second embodiment in this paragraph further comprising openings in the baffle for emitting stripping gas to fluidize catalyst above the baffle. An embodiment of the invention is one, any or all of prior embodiments in this paragraph up through the second embodiment in this paragraph wherein the top horizontal wall of the tunnel overhangs the baffle and the tunnel defines an inverted U lacking a horizontal wall opposing the top horizontal wall so as to channel catalyst over the baffle as it enters the disengaging chamber from the reactor annulus. An embodiment of the invention is one, any or all of prior embodiments in this paragraph up through the second embodiment in this paragraph wherein the baffle extends from an intersection of the disengaging chamber with the reactor annulus. An embodiment of the invention is one, any or all of prior embodiments in this paragraph up through the second embodiment in this paragraph further comprising a vertical weir depending from the baffle.

A third embodiment of the invention is an apparatus for separating catalyst particles from a gaseous product stream comprising an elongated riser in which a hydrocarbon feed is contacted with catalyst particles to produce a gaseous product, the riser including an outlet to discharge the solid catalyst particles and gaseous products into a disengaging chamber, the disengaging chamber including an outer shell and a lower stripping section comprising stripping internals; a passage communicating the disengaging chamber with a reactor annulus and a deflecting baffle extending from an intersection of the disengaging chamber with the reactor annulus into the disengaging chamber. An embodiment of the invention is one, any or all of prior embodiments in this paragraph up through the third embodiment in this paragraph wherein a lower edge of the passage is located just above the intersection. An embodiment of the invention is one, any or all of prior embodiments in this paragraph up through the third embodiment in this paragraph further comprising a gas distributor located directly below the deflecting baffle.

A fourth embodiment of the invention is a process for separating catalyst particles from a gaseous product stream comprising contacting a hydrocarbon feed stream with catalyst particles in an elongated riser to produce gaseous products; discharging the catalyst particles and gaseous products from the riser into a disengaging chamber; disengaging catalyst particles from the gaseous product; passing catalyst particles and gaseous products from a passage to a reactor annulus into the disengaging chamber; and deflecting downward movement of the catalyst particles laterally upon entering into the disengaging chamber from the passage.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for separating catalyst particles from a gaseous product stream comprising: contacting a hydrocarbon feed stream with catalyst particles in an elongated riser to produce gaseous products; inducing the catalyst particles and gaseous products to swirl in an angular direction upon exiting said riser and entering a disengaging chamber to disengage catalyst particles from said gaseous product; inhibiting said catalyst particles and gaseous products from exiting said disengaging chamber and entering a reactor annulus.

2. The process of claim 1 further comprising requiring passage of said catalyst particles and said gaseous products through a tunnel with a vertical wall to exit said disengaging chamber and enter said reactor annulus.

3. The process of claim 2 wherein said vertical wall of said tunnel presents a face opposed to the angular direction in which the catalyst particles and gaseous products swirl.

4. The process of claim 1 further comprising: stripping descending catalyst particles with a stripping gas over elongated strips in a stripping section; and separating catalyst particles entrained with ascending gaseous products from said gaseous products.

5. The process of claim 4 further comprising deflecting downward movement of said catalyst particles laterally upon entering into said disengaging chamber from said tunnel.

6. The process of claim 5 further comprising fluidizing said catalyst particles being deflected with fluidizing gas through openings in a deflecting baffle.

7. An apparatus for separating catalyst particles from a gaseous product stream comprising: an elongated riser in which a hydrocarbon feed is contacted with catalyst particles to produce a gaseous product, said riser including a swirl outlet configured to induce the solid catalyst particles and gaseous products to swirl in an angular direction to disengage catalyst particles from said gaseous product; a disengaging chamber communicating with said swirl outlet of said riser, said disengaging chamber including an outer shell and a stripping section comprising stripping internals; a tunnel comprising a vertical wall which communicates said disengaging chamber with a reactor annulus.

8. The apparatus of claim 7 wherein said vertical wall extends inwardly of said shell.

9. The apparatus of claim 7 wherein said tunnel comprises a first vertical wall and a second vertical wall.

10. The apparatus of claim 9 wherein the first vertical wall is wider than the second vertical wall.

11. The apparatus of claim 9 wherein said first wall extends more outwardly of said shell and said second wall extends more inwardly of said shell.

12. The apparatus of claim 9 wherein said tunnel comprises a top horizontal wall upwardly of said first vertical wall and said second vertical wall.

13. The apparatus of claim 12 further comprising a baffle below said tunnel that extends into said disengaging chamber at a downward incline.

14. The apparatus of claim 13 further comprising openings in said baffle for emitting stripping gas to fluidize catalyst above said baffle.

15. The apparatus of claim 13 wherein said top horizontal wall of said tunnel overhangs said baffle and said tunnel defines an inverted U lacking a horizontal wall opposing said top horizontal wall so as to channel catalyst over said baffle as it enters said disengaging chamber from said reactor annulus.

16. The apparatus of claim 15 wherein said baffle extends from an intersection of said disengaging chamber with said reactor annulus.

17. The apparatus of claim 13 further comprising a vertical weir depending from said baffle.

18. An apparatus for separating catalyst particles from a gaseous product stream comprising: an elongated riser in which a hydrocarbon feed is contacted with catalyst particles to produce a gaseous product, said riser including an outlet to discharge the solid catalyst particles and gaseous products into a disengaging chamber, said disengaging chamber including an outer shell and a lower stripping section comprising stripping internals; a passage communicating said disengaging chamber with a reactor annulus and a deflecting baffle extending from an intersection of said disengaging chamber with said reactor annulus into said disengaging chamber.

19. The apparatus of claim 18 wherein a lower edge of said passage is located just above said intersection.

20. The apparatus of claim 18 further comprising a gas distributor located directly below said deflecting baffle.

* * * * *